United States Patent
Shin et al.

(10) Patent No.: US 6,878,158 B2
(45) Date of Patent: Apr. 12, 2005

(54) PROCESS FOR COUPLING AN ANGIOPLASTY STENT TO A CORRESPONDING INSERTION ELEMENT, AND KIT THUS FORMED

(75) Inventors: Dong Shin, Poway, CA (US); Vincenzo Cassolaro, Saluggia (IT); Andrea Mariotto, Turin (IT)

(73) Assignee: Sorin Biomedica Cardio S.p.A., Saluggia (IT)

( * ) Notice: Subject to any disclaimer, the term of this patent is extended or adjusted under 35 U.S.C. 154(b) by 190 days.

(21) Appl. No.: 09/852,988

(22) Filed: May 10, 2001

(65) Prior Publication Data

US 2002/0007207 A1 Jan. 17, 2002

(30) Foreign Application Priority Data

Jul. 11, 2000 (IT) ...................................... TO2000A0692

(51) Int. Cl.$^7$ .................................................. A61F 2/06

(52) U.S. Cl. ..................... 623/1.11; 623/1.23; 606/108; 604/96.01

(58) Field of Search ............................. 623/1.11, 1.12, 623/1.23, 108, 96.01

(56) References Cited

U.S. PATENT DOCUMENTS

| | | | |
|---|---|---|---|
| 5,591,222 A | | 1/1997 | Susawa et al. |
| 5,693,066 A | * | 12/1997 | Rupp et al. .................. 606/198 |
| 5,725,519 A | | 3/1998 | Penner et al. |
| 5,807,398 A | * | 9/1998 | Shaknovich ................. 606/108 |
| 5,810,838 A | | 9/1998 | Solar |
| 5,817,100 A | * | 10/1998 | Igaki ........................... 623/1.11 |
| 5,860,966 A | | 1/1999 | Tower |
| 5,893,852 A | | 4/1999 | Morales |
| 5,911,452 A | | 6/1999 | Yan |
| 5,911,752 A | * | 6/1999 | Dustrude et al. ............. 623/1.1 |
| 5,913,871 A | | 6/1999 | Werneth et al. |
| 6,009,614 A | | 1/2000 | Morales |
| 6,018,857 A | | 2/2000 | Duffy et al. |
| 6,024,737 A | | 2/2000 | Morales |
| 6,027,510 A | * | 2/2000 | Alt ............................... 606/108 |
| 6,051,002 A | | 4/2000 | Morales |
| 6,063,092 A | | 5/2000 | Shin |
| 6,068,635 A | * | 5/2000 | Gianotti ....................... 606/108 |
| 6,149,680 A | * | 11/2000 | Shelso et al. ............... 623/1.11 |
| 6,322,586 B1 | * | 11/2001 | Monroe et al. ............. 623/1.11 |
| 6,585,747 B1 | * | 7/2003 | Limon et al. ................ 606/198 |
| 6,660,031 B2 | * | 12/2003 | Tran et al. .................. 623/1.12 |

FOREIGN PATENT DOCUMENTS

| | | |
|---|---|---|
| DE | 42 35 004 | 4/1993 |
| DE | 19532288 | 3/1997 |
| EP | 0697226 A1 | 2/1996 |
| EP | 0 855 171 A2 | 7/1998 |
| EP | 0 873 731 B1 | 10/1998 |
| EP | 0 897 730 A2 | 2/1999 |

(Continued)

OTHER PUBLICATIONS

Search report for counterpart European Patent Application 01830230.7 (2 pages).

Primary Examiner—David H. Willse
Assistant Examiner—Javier G. Blanco
(74) Attorney, Agent, or Firm—Popovich, Wiles & O'Connell, P.A.

(57) ABSTRACT

A process for setting an angioplasty stent on a corresponding insertion element, such as a delivery catheter, in which the angioplasty stent is subjected to an action of radial contraction. The stent is in a radially contracted state before being placed on the insertion element. Preferably, radial contraction of the stent results in a diameter at least marginally smaller than the diameter of the insertion element, e.g., a balloon catheter. After the stent has been set on the insertion element, in the structure of the stent there remain residual states of constraint which act in the direction of securing the stent in the condition of coupling to the insertion element.

13 Claims, 2 Drawing Sheets

FOREIGN PATENT DOCUMENTS

| | | |
|---|---|---|
| EP | 0 901 776 A1 | 3/1999 |
| EP | 0 903 122 A2 | 3/1999 |
| EP | 0 916 318 A1 | 5/1999 |
| EP | 0 916 319 A2 | 5/1999 |
| WO | WO 99/15106 | 1/1999 |
| WO | WO 00/06052 | 10/2000 |

* cited by examiner

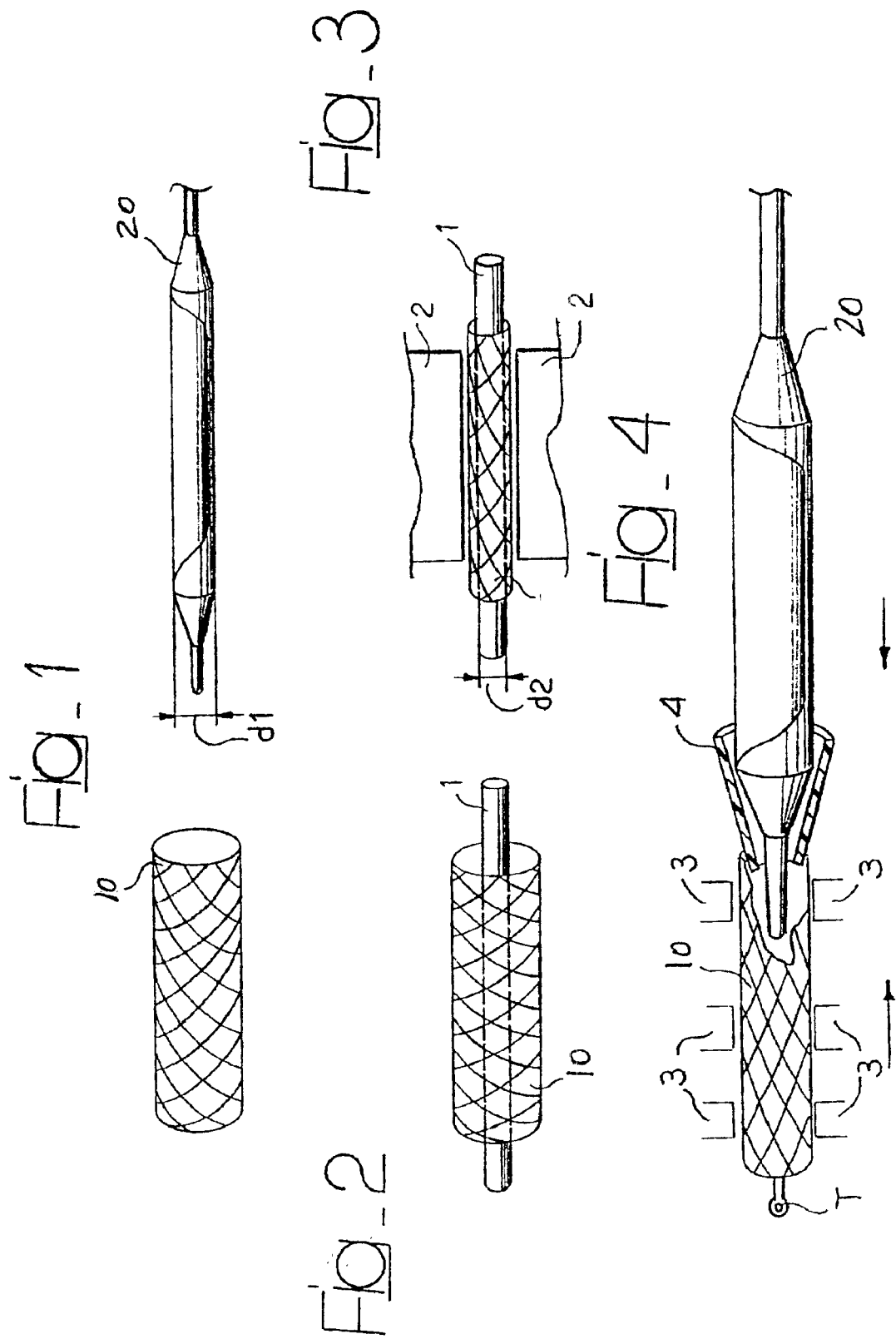

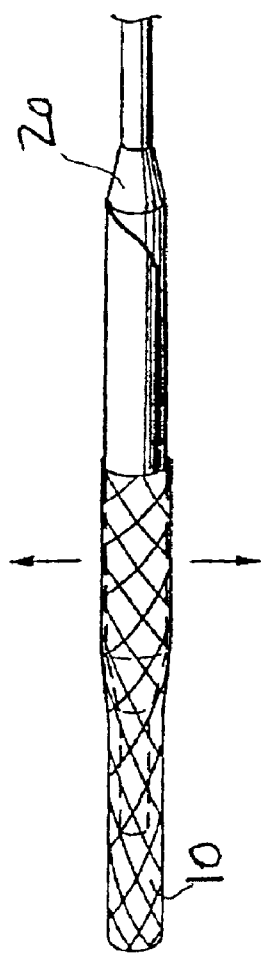
Fig_5
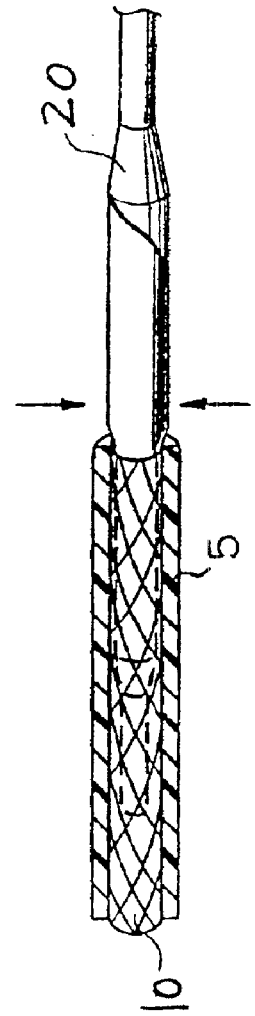
Fig_6
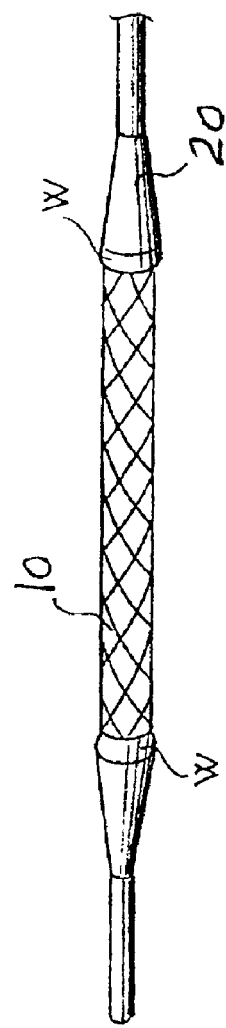
Fig_7

PROCESS FOR COUPLING AN ANGIOPLASTY STENT TO A CORRESPONDING INSERTION ELEMENT, AND KIT THUS FORMED

FIELD OF THE INVENTION

The present invention relates to angioplasty stents. In particular, this invention relates to coupling a stent to an insertion element that may be used for location and deployment of the stent in situ.

BACKGROUND OF THE INVENTION

The solution currently most frequently adopted (which is the solution to which reference will be made by way of example in the remainder of the present description) envisions that the insertion element is represented by a catheter provided with a balloon part. Once the stent has been brought to the site of implantation by a catheter, it is possible to deploy the stent by distending the balloon. That is, the stent is brought from its radially contracted condition to its radially expanded or extended condition, in which the stent performs the desired action of stenting on the portion of the vessel being treated.

Formerly, it was common to crimp the stent onto the insertion element (typically a catheter) just prior to the implantation intervention. This was carried out by means of an operation which was usually entrusted to a doctor and/or to the staff that performed the implantation operation. Subsequently, the solution that has increasingly gained ground is one in which the stent is mounted on the insertion element as final step, carried out at an industrial level, of the process of preparation of an implantation kit consisting of the stent already mounted directly on the insertion element.

The problems linked to coupling the stents to the corresponding insertion elements are numerous but essentially amount to a number of basic requirements, namely:

- the coupling operation must be sufficiently quick and convenient;
- the operation must not have adverse effects on the operating characteristics either of the stent or of the insertion element; and
- the coupling must be absolutely firm and secure, in such a way as to rule out completely any risk of the stent possibly being undesirably separated from the insertion element, it being necessary for separation to occur (and moreover in a precise and reliable way) only after the stent has been properly positioned and deployed in the site being treated.

The prior art regarding coupling of stents to corresponding insertion elements is highly extensive. For example, from U.S. Pat. No. 5,725,519 a solution is known in which a tube, pre-installed together with a stent, is fixed to a component having a tension formation. The tube with the stent extends into the cavity of a second component, which is also provided with a tension formation. The hole of the second component is conical and has a tapered cross section in the direction of the first component. By acting on the two components in the direction that causes them to be moved away from one another, it is possible to pass the tube through the conical hole, so reducing the diameter of the stent, and hence bringing about its radial contraction and coupling onto the insertion element consisting of a balloon catheter.

U.S. Pat. No. 5,911,452 (see also EP-A-0 867 156) describes the use of a casing with an inner chamber traversed by a flexible tube. The stent is positioned inside a median portion of the flexible tube and the balloon part of the catheter is inserted into the flexible tube, located inside the stent. A fluid under pressure is injected into the aforesaid chamber which compresses the flexible tube in a circumferential direction, simultaneously compressing the stent so as to grip it (i.e., crimp it) onto the catheter balloon.

From EP-A-0 903 122, a gripping or crimping tool is known formed by a cylindrical element provided with an external thread and by a rotating collar with an internal thread which engages the aforesaid external thread. The neck part of the cylindrical element is subdivided into a series of jaws subjected to a bias in the direction of expansion. The stent, which is set on the balloon catheter and placed inside the aforesaid jaws in an open condition, undergoes a crimping operation when the aforesaid collar is made to rotate and advance towards the jaws.

EP-A-0 873 731 describes a device provided with a set of oscillating-arm parts, as well as an annular or tubular element associated to the aforesaid parts. The element in question has an opening, which is on the whole cylindrical and is uniformly compressible in a radial direction inwards when the arm parts oscillate downwards starting from the intermediate portion. In this way it is possible to crimp the stent onto the insertion element.

EP-A-0 916 318 describes another crimping tool comprising a tapered tube mounted coaxially on the catheter in a position adjacent to the distal end of the stent. The aforesaid tube, which can be peeled off, has a first diameter greater than the diameter of the stent, as well as a second diameter smaller than the diameter of the stent prior to crimping. By sliding the tube onto the stent, a radial force is applied, directed inwards, which is distributed evenly on the circumference.

From EP-A-0 916 319 yet another crimping tool is known comprising supporting elements set at a distance apart, as well as a helical spring applied at one end to a stem and at the opposite end to one of the supports. The stent/balloon catheter ensemble is inserted into the axial cavity of the spring, with the result that the spring carries out crimping of the stent.

U.S. Pat. No. 5,893,852 describes another apparatus comprising a cylindrical casing made up of two co-operating parts. The stent, which is mounted on the balloon, is inserted in a cylindrical cavity the distal part of which has a conical end. The stent is compressed and crimped on the balloon by means of screwing of the two aforesaid parts.

U.S. Pat. No. 5,860,966 describes yet another apparatus comprising a casing with a cylindrical membrane that is closed at both ends so as to form a fluid-tight chamber between the membrane and the casing. A fluid is introduced under pressure into the chamber which acts on the membrane until it brings the membrane into a condition of pressure contact with the stent so as to force the stent into a condition of engagement on the balloon.

From U.S. Pat. No. 5,810,838 a solution is known that is based upon the use of a hollow chamber defining a space designed to be filled with fluid and of a compliant tubular sleeve set inside the chamber with one open end communicating with the outside of the casing. The stent is positioned on the corresponding catheter and inserted into the sleeve. The fluid is pressurized so as to compress the sleeve and the stent radially.

U.S. Pat. No. 6,009,614 describes a device is known which comprises a cylindrical rigid frame inside which an elastic tube is set. The stent, already mounted on the balloon, is inserted in an opening of the frame. The elastic tube is subjected to axial pressure so as to reduce its length and increase its thickness in the radial direction to effect crimping of the stent.

U.S. Pat. No. 6,018,857 describes a tool comprising a grip from which there extends a tube. The stent is set around the tube and is mounted on the balloon by gripping the tool grip and acting in a direction where the grip is pushed away from the catheter. WO-A-00/06052 discloses a crimping tool comprising a stationary plate and a sliding-platform element. A closing plate is hinged to the sliding platform so as to partially overlap the stationary plate in a lowered position. The stent, which is already slightly crimped by hand, is set on the stationary plate starting from a lateral position. The closing plate is displaced into the lowered position so as to withhold the stent in such a way that an external force applied on the closing plate, in combination with the movement of translation of the closing plate itself, produces crimping of the stent.

U.S. Pat. No. 6,024,737 describes a device that has a compressible bend part that can be compressed in a radial direction inwards so as to obtain crimping of the stent and U.S. Pat. No. 6,051,002 describes a device is known which comprises a pair of grips that form a bend part for withholding the ensemble made up of the stent and the catheter. The ends of the bend are displaced in opposite directions, so reducing the radial dimensions of the bend to crimp the stent on the balloon.

Yet other documents envision the possibility of using methods of thermal treatment (so-called "annealing"): in this connection see, for instance, WO-A-99/15106 and U.S. Pat. No. 6,063,092.

Yet other documents specifically tackle the problem of preventing relative sliding between the stent and the catheter. In this connection see, for example, U.S. Pat. No. 5,893,852 (previously cited), U.S. Pat. No. 5,913,871, EP-A-0,855,171, EP-A-0,897,730 and EP-A-0,901,776.

SUMMARY OF THE INVENTION

The purpose of the present invention is to provide a further improvement of the solutions described previously, in particular regarding the complete reliability of the coupling between the stent and the insertion element and the possibility of conferring an extremely reduced profile on the ensemble made up of the stent and the insertion element on which the stent is crimped.

Both of the characteristics referred to above are of particular importance and interest, above all as regards the methods of direct stenting.

In one aspect, this invention is a method of loading a stent on a delivery catheter, the delivery catheter having a proximal end and a distal end, comprising providing a stent having a length, at least a portion of the length of the stent being in a radially contracted position, the stent capable of being dilated from the radially contracted position to a radially expanded position, the stent having a first diameter in the radially contracted position and a second diameter in the radially expanded position, the second diameter being greater than the first diameter; providing the delivery catheter; and mounting the stent, while in the radially contracted position, onto the delivery catheter. The delivery catheter may be a balloon catheter. In one embodiment, the catheter may have a third diameter, the first diameter being smaller than the third diameter. The first diameter may be smaller than the third diameter by at least 5% or at least 25%. The mounting step may also comprise providing a means for radial containment of the stent. The stent may be formed from steel. The entire length of the stent may be in the radially contracted position. The stent may be radially contracted by forcing the stent into contact with a forming stem.

In a second aspect, this invention is a method of loading a stent on a delivery catheter, the delivery catheter having a proximal end and a distal end, comprising: providing a stent having a length, at least a portion of the length of the stent being in a radially contracted position, the stent capable of being dilated from the radially contracted position to a radially expanded position, the stent having a first diameter in the radially contracted position and a second diameter in the radially expanded position, the second diameter being greater than the first diameter; providing the delivery catheter; providing a conical sheath disposed about the distal end of the delivery catheter; and sliding the stent in the radially contracted position over the conical sheath onto the delivery catheter.

The conical sheath may be formed from a material having a low coefficient of friction, a flexible material, or polytetrafluoroethylene. The method may further include removing the conical sheath after the stent has been mounted on the delivery catheter. The stent may slide onto the delivery catheter by placing tension on the distal end of the delivery catheter so that it is pulled into the stent.

In a third aspect, this invention is a method of loading a stent on a delivery catheter, the delivery catheter having a proximal end and a distal end, comprising: providing a stent having a length, at least a portion of the length of the stent being in a radially contracted position, the stent capable of being dilated from the radially contracted position to a radially expanded position, the stent having a first diameter in the radially contracted position and a second diameter in the radially expanded position, the second diameter being greater than the first diameter; providing the delivery catheter; and mounting the stent in the radially contracted position onto the delivery catheter such that the stent is radially expanded during the mounting step to a delivery position, the stent in the delivery position having a delivery diameter, the delivery diameter being greater than the first diameter and less than the second diameter. The delivery catheter may have a third diameter, such that the first diameter and the delivery diameter are smaller than the third diameter. The first diameter may smaller than the third diameter by at least 5% or at least 25%. In the mounting step, radial contraction of the delivery catheter may occur.

In a fourth aspect, this invention is a method of loading a stent on a delivery catheter, the delivery catheter having a proximal end and a distal end, comprising: providing a stent having a length, at least a portion of the length of the stent being in a radially contracted position, the stent capable of being dilated from the radially contracted position to a radially expanded position, the stent having a first diameter in the radially contracted position and a second diameter in the radially expanded position, the second diameter being greater than the first diameter; providing the delivery catheter; providing a conical sheath disposed about the distal end of the delivery catheter; and sliding the stent in the radially contracted position over the conical sheath onto the delivery catheter such that the stent is expanded to a delivery position, the stent in the delivery position having a delivery diameter, the delivery diameter being greater than the first diameter and less than the second diameter.

In a fifth aspect, this invention is a stent delivery system comprising: a delivery catheter; and a stent having a length, at least a portion of the length of the stent being in a radially contracted position, the stent capable of being dilated from the radially contracted position to a radially expanded position, the stent having a first diameter in the radially contracted position and a second diameter in the radially expanded position, the first diameter being smaller than the second diameter; the stent being mounted on the delivery catheter in a manner that results in the stent being expanded to a delivery position having a delivery diameter, the delivery diameter being greater than the first diameter, the stent being comprised of a material that, when expanded from the contracted position to the delivery position during mounting, results in the stent having at least one state of constraint acting in the direction of radial contraction from the delivery position to the contracted position.

In a sixth aspect, this invention is a kit for the delivery of a stent, comprising: a delivery catheter having a proximal end and a distal end; a conical sheath configured to be disposed about the distal end of the delivery catheter; and a stent having a length, at least a portion of the length of the stent being in a radially contracted position, the stent capable of being dilated from the radially contracted position to a radially expanded position; wherein the stent is configured to be mounted onto the delivery catheter by fitting the stent in the radially contracted position over the conical sheath.

BRIEF DESCRIPTION OF THE DRAWINGS

FIG. 1 is a perspective view of a stent in its expanded configuration and an insertion element prior to coupling.

FIG. 2 is a perspective view of the stent of FIG. 1 in an expanded configuration mounted on a stem.

FIG. 3 is a perspective view of the mounted stent of FIG. 2 in a radially compressed configuration.

FIG. 4 is a perspective view showing the stent in position to be mounted on the insertion element.

FIG. 5 is a perspective view showing the stent partially mounted on the insertion element.

FIG. 6 is a perspective view showing the stent partially mounted on the insertion element and held by a containment element.

FIG. 7 is a perspective view of the stent mounted on the insertion element ready for use.

DESCRIPTION OF THE PREFERRED EMBODIMENTS

As is well known (the literature on this subject also in the field of patents is truly imposing), by the term "angioplasty stent" is indicated in general a device having an overall tubular shape which may be introduced in a radially contracted position inside a vessel (typically a blood vessel) affected by stenosis. The subsequent expansion of the stent in the radial direction produces widening of the vessel, with consequent elimination of the stenosis and maintenance of the vessel in a condition of patency as a result of the action of support exerted by the stent.

In the figures, reference 10 designates an angioplasty stent. Stent 10 is therefore illustrated in an altogether schematic way, where only the envelope corresponding to a generic cylindrical tubular form is represented.

In FIG. 1, it is assumed that stent 10 illustrated has radial dimensions corresponding to those that it has at the end of its process of formation, whatever that process may be. The diameter of stent 10 may also be smaller than the diameter that it assumes as a result of its deployment in the implantation site.

The solution according to the invention is in fact suitable for being used with practically any type of stent, in a way altogether irrespective of:

the geometrical and structural characteristics of the stent;

the criteria of fabrication of the stent (for example, whether the stent is obtained starting from a microtube (so-called hypotubing) or by winding/weaving of yam; and the possible treatments to which the stent itself may or must be subjected prior to or following upon coupling to the insertion element, generically designated by 20 in the Figures.

The same considerations mentioned previously also apply as regards the material with which the stent has been made. The experiments conducted by the applicant show, however, that the solution according to the invention is suitable for being used to particular advantage in combination with stents made starting from a steel-based material.

Substantially similar considerations regarding the possibilities of use—which are moreover altogether general—of the solution according to the invention apply also to insertion element 20, here represented schematically (with reference to the solution most widely used, at least at present) at the distal-end part of a balloon catheter.

In view of the envisioned coupling of stent 10 to the balloon part, in what follows this part will in practice be identified with insertion element 20. It is, on the other hand, altogether evident for a person skilled in the art that the insertion element comprises, in association with the part illustrated, also other elements (not illustrated in the drawings, but altogether known in the prior art) that enable the insertion element 20, along with stent 10 mounted thereon, to be guided onto the implantation site in view of its subsequent deployment, this too being obtained according to known criteria.

For the purposes of the present invention, it will be sufficient to note that the insertion element 20 (however made) has in general a diameter d1, which will be assumed, in what follows, as being substantially constant, it hence being also assumed that the insertion element 20 has a circular or substantially circular section.

As represented in the figures, element 20 corresponds to the typical configuration of winding of the balloon part of a catheter prior to deployment thereof. The reference to this example of embodiment renders altogether evident to a person skilled in the art the fact that, albeit substantially constant, the diameter identified by the value d1 may in actual fact present, at least at a local level, slight variations due to the characteristics of winding of the balloon.

The first step of the process according to the invention envisions that stent 10, which is not yet coupled to insertion element 20, is subjected to an action of radial contraction such as to bring its internal diameter to a value d2 at least marginally smaller than the external diameter d1 of the insertion element 20 to which stent 10 is to be coupled.

This result may be obtained, for example (the person skilled in the art will appreciate immediately that it is possible to resort to other functionally equivalent solutions) by fitting stent 10 on a pin or stem 1 consisting, for instance, of a cylindrical body made of rigid or substantially rigid material having an external diameter equal to d2 and, preferably, a cylindrical cross section.

The operation of radial compression of stent 10 aimed at bringing the internal diameter thereof to the value d2 is schematically illustrated in the sequence of FIGS. 2 and 3.

As an alternative to the solution described herein, purely by way of example, the aforesaid action of radial contraction may be obtained with any known solution, including the various solutions cited in the introductory part of the present description, and this, even though the previous solutions are in actual fact aimed at obtaining radial contraction of stent 10 so as to bring about its crimping directly on the insertion element.

On the other hand, with the solution according to the invention, the action of radial contraction is performed before stent 10 is coupled to the insertion element 20.

As regards what is to be understood, with reference to the diameter d2, by diameter "at least marginally smaller" than the diameter of the insertion element 20, the experiments conducted by the applicant show that, even though the results of the invention may be achieved for any value of d2 smaller than d1, particularly advantageous results are achieved when the diameter d2 is at least 5% smaller than the diameter d1. Particularly satisfactory results may be achieved (above all with reference to stents made of steel-based materials) when the diameter d2 is approximately 25% smaller than the diameter d1.

Without wishing to be tied down to any specific theory in this regard, the applicant has reason to believe that, if said preferred values are chosen, as a result of the radial contraction or compression of stent 10, there will arise, following upon the subsequent operation of application on the insertion element 20 (an operation that may be carried out according to criteria described in greater detail in what follows) states of constraint of particular importance, which are able to ensure the desired degree of coupling of stent 10 to element 20.

There exists of course the possibility that the action of radial contraction of stent 10, here represented as performed by gripping of stent 10 on the pin or stem 1, is obtained and/or is accompanied by a possible heat treatment.

FIG. 3 refers, in deliberately schematic terms, to a solution in which the operation that leads to a reduction in the radial dimensions of stent 10 so that the external diameter of the latter corresponds to the value d2 is obtained as a result of an action of radial compression which is assumed as being ideally distributed in a uniform way over the entire periphery of stent 10 and as being obtained by means of radial-compression tools 2.

As has already been said, the above tools may be made, for example, according to the same general criteria described in various documents of the prior art cited in the introductory part of the present description.

From FIG. 3 it will be noted that tools 2 have been deliberately represented as "shorter" than the overall axial extension of stent 10, hence such as not to involve the ends of stent 10 directly in their action.

The above representation, which is deliberately schematic, intends to recall the fact that the aforesaid operation of reducing the radial dimensions does not need to be performed over the entire development of stent 10, but may involve just one part of stent 10, for example the central portion (as in the embodiment illustrated herein), or just the end portions (this according to an arrangement which is complementary with respect to the one illustrated in FIG. 3), or even one or more portions the dimensions of which and/or the distribution of which over the length of the stent are determined, among other things, according to the characteristics of stent 10 and/or of element 20.

Again regarding the aforesaid applicational requirements, it is possible, according to a further variant embodiment of the invention (not specifically illustrated in the drawings), to cause the action of reduction of the internal diameter to the value d2 to involve only certain portions of the peripheral development of stent 10, and not the entire circumference thereof.

In the latter case, for example, tool or tools 2 in practice assume the form of punches designed to advance radially towards the body of stent 10 so as to produce reduction of the internal diameter of the latter to the value d2 only in those areas that are affected by the action of the punches.

In any case it will be appreciated that an important characteristic of the solution according to the invention is represented by the fact that the action of radial contraction of stent 10 designed to bestow on the stent itself dimensions such as to enable its coupling on insertion element 20 is performed prior to, and not after, mounting of stent 10 on element 20.

The subsequent steps of the process according to the invention thus envision that stent 10, the internal diameter of which has been brought to the value d2, is then fitted onto insertion element 20, the external diameter of which is equal to d1.

The foregoing is carried out in conditions in which the diameter d2 is "at least marginally smaller" than the diameter d1. For the meaning attributed to the term "at least marginally smaller", refer to the note of a terminological nature expressed previously.

As in the case of the operation of reduction of the internal diameter of stent 10 to the value d2, in order to set the stent 10 on the insertion element 20 it is possible to resort to various solutions, all of which are in themselves known.

The sequence of FIGS. 4 and 5, on the one hand, and FIGS. 4 and 6, on the other, refer to two possible solutions which have been tested with successful results by the present applicant and which are essentially based upon causing stent 10 to advance longitudinally with respect to insertion element 20 as a result of a relative movement of sliding.

The aforesaid movement may be obtained, for example, by "feeding" distal end T of the catheter, of which element 20 forms part, inside stent 10, and then exerting, on distal end T, a careful tensile action (by means of a tool not specifically illustrated but of a type in any case known, for instance of the nature of some of the solutions described in the documents cited in the introductory part). During this process, stent 10 is withheld (by an equally careful action of retention in order to prevent the stent getting damaged) by means of tools 3, which are also of a conventional type.

As has already been said, the above-mentioned movement of insertion derives from a relative motion of stent 10 and element 20. This movement may therefore be obtained either by holding the stent 10 stationary and sliding element 20 inside it, or by holding element 20 stationary and sliding elements 3 which carry stent 10 with them causing stent 10 to slide onto the outside of element 20, or again by means of a movement involving both element 20 and stent 10 together.

In particular, the action of "feeding" of stent 10 onto element 20 is preferably facilitated by means of a coupling insert 4 which may, for example, consist of a sort of sheath which comprises a portion having a conical shape or the shape of a truncated cone and is made of a material having a low coefficient of friction (for example, polytetrafluoroethylene or similar materials) and a reasonable degree of flexibility, also in relation to its thickness.

Insert 4 is set on the end of element 20 starting from which the sliding movement of stent 10 onto element 20 is performed.

It will moreover be appreciated that, in the case where element 20 is made up of the balloon of a catheter, element 4 (which is generally eliminated and removed once the desired coupling of stent 10 and of element 20 has been achieved) has a shape that adapts to the approximately conical, or anyway tapered, shape which the aforementioned end of the balloon normally already has in any case (see, for example the right-hand part of FIG. 1).

FIGS. 5 and 6 show the action of coupling between stent 10 and element 20 consists essentially in two possible effects which can be exploited both as alternatives and in combination, according to the specific application requirements.

In particular, FIG. 5 refers to a situation in which while stent 10 is being fitted onto element 20 it is not subjected to an action of containment in a radial direction.

Since, as has already been seen, the internal diameter d2 of stent 10 is at least marginally smaller than the external diameter d1 of element 20, in these conditions the coupling movement is performed (assuming, from a purely conceptual standpoint, that element 20 is radially incompressible) as a result of a slight radial expansion of stent 10 which brings the internal diameter of the latter from the value d2 to the value d1.

FIG. 6 illustrates, during the aforesaid movement of insertion, that stent 10 undergoes an action of radial containment, for instance by setting on it sheath 5 (designed so that it can subsequently be removed). Sheath 5 comprises a materials such as, for example silicon rubber, polyurethane, or polytetrafluoroethylene. Sheath 5 may vary in thickness and prevents, or at least substantially prevents, radial dilation of stent 10.

In the above situation, the coupling action is achieved as a result of a radial contraction of element 20, the external diameter of which passes from value d1 to value d2.

The intrinsic physical characteristics of the elements concerned mean that, in practice, at least in the case represented in FIG. 5, in which stent 10 is not subjected to an action of radial containment, the desired coupling involves both a radial expansion of stent 10 and a radial compression of element 20. In the final coupling condition, the internal diameter of stent 10 and the external diameter of element 20 end up coinciding with one another at a value which is intermediate between values d1 and d2.

The same may apply also in the case of the solution of FIG. 6, at least in those cases in which the action of containment represented as exerted by sheath 5 is not absolute but is in any case such as to enable an albeit modest dilation of stent 10.

Where the aim is in any case to minimize the end profile of mounting of the stent 10 on element 20, it may be desirable for the above-mentioned action of radial containment of stent 10 to be absolute; consequently, the movement of insertion is performed exclusively by means of a radial contraction of element 20. Of course, once containment element 5 is removed, the elastic reaction of element 20 aimed at producing radial expansion of the latter, is in any case such as to bring about a corresponding expansion, albeit of an extremely contained amount, of stent 10.

In any case, once the final condition of coupling has been reached, as represented in FIG. 7, stent 10 is held on insertion element 20 principally as a result of the states of constraint existing within the structure of stent 10, which tend to bring stent 10 back towards the condition imparted on it following upon the operation represented in FIG. 3, i.e., following upon the action of radial contraction that brought its internal diameter to value d2, which is smaller than the value of diameter d1 of element 20 on which stent 10 was subsequently fitted.

The tests carried out by the applicants show that, above all in the case where diameter d2 is at least 5% smaller, and preferably approximately 25% smaller, than diameter d1, the intensity of the forces deriving from the above-mentioned states of constraint is somewhat marked, and hence such as to ensure a firm anchorage of stent 10 on element 20 and such in any case as to prevent undesirable separation of stent 10 from element 20, also in view of the possible performance of direct-stenting interventions. The foregoing is achieved without any need to resort to further forms of treatment, such as heat treatment, of the mounted stent 10 as shown in FIG. 7.

Persons skilled in the art will immediately appreciate that in the solution according to the prior art, where to achieve coupling with element 20, the stent is subjected to radial compression after being mounted on element 20 or while it is being mounted on element 20, the residual states of constraint that remain in stent 10 act in an exactly opposite direction, producing a mechanism of elastic return which tends to dilate stent 10, bringing its radial dimensions back towards the value that these dimensions had before stent 10 was compressed on element 20.

Consequently, in such solutions according to the prior art, the states of constraint tend, at least in a latent way, to operate in the direction of favouring separation of stent 10 from element 20.

Instead, in the solution according to the invention, the above states of constraint tend to bring stent 10 towards the radially contracted position (i.e., towards internal diameter d2) which had previously been imparted on it during the step represented in FIG. 3. The aforesaid states of constraint thus act in the direction of favouring anchorage of stent 10 on the insertion element 20. At the same time, the process facilitates, if indeed it does not actually produce spontaneously, the formation of swollen end portions W of element 20 (which is usually made of elastic material, such as silicon rubber or the like) such as to perform a further action of longitudinal containment of the stent 10 on element 20.

Without prejudice to the principle of the invention, the details of construction and the embodiments may vary widely with respect to what is described and illustrated herein, without thereby departing from the scope of the present invention.

What is claimed is:

1. A method of loading a stent on a delivery catheter, the delivery catheter having a proximal end and a distal end, the method comprising:

providing a stent having a length, at least a portion of the length of the stent being in a radially contracted position, the stent capable of being dilated from the radially contracted position to a radially expanded position, the stent having a first diameter in the radially contracted position and a second diameter in the radially expanded position, the second diameter being greater than the first diameter; providing the delivery catheter the delivery catheter having a third diameter, the first diameter being smaller than the third diameter;

providing a conical sheath disposed about the proximal end of the delivery catheter;

sliding the stent in the radially contracted position over and past the conical sheath onto the delivery catheter.

2. The method of claim 1, wherein the first diameter is smaller than the third diameter by at least 5%.

3. The method of claim 1, wherein the first diameter is smaller than the third diameter by at least 25%.

4. A method of loading a stent on a delivery catheter, the delivery catheter having a proximal end and a distal end, the method comprising:

providing a stent having a length, at least a portion of the length of the stent being in a radially contracted position, the stent capable of being dilated from the radially contracted position to a radially expanded position, the stent having a first diameter in the radially contracted position and a second diameter in the radially expanded position, the second diameter being greater than the first diameter;

providing the delivery catheter;

providing a conical sheath disposed about the distal end of the delivery catheter;

sliding the stent in the radially contracted position over the conical sheath onto the delivery catheter such that the stent is expanded to a delivery position, the stent in the delivery position having a delivery diameter, the delivery diameter being greater than the first diameter and less than the second diameter.

5. The method of claim 4, wherein the step of providing the conical sheath comprises providing the conical sheath formed from a material having a low coefficient of friction.

6. The method of claim 4, wherein the step of providing the conical sheath comprises providing the conical sheath formed from a flexible material.

7. The method of claim 4, wherein the step of providing the conical sheath comprises providing the conical sheath formed from polytetrafluoroethylene.

8. The method of claim 4, further comprising the step of removing the conical sheath after the stent has been mounted on the delivery catheter.

9. The method of claim 4 wherein, in the step of providing the delivery catheter, the delivery catheter has a third diameter, the first diameter and delivery diameter being smaller than the third diameter.

10. The method of claim 9, wherein the first diameter is smaller than the third diameter by at least 5%.

11. The method of claim 9, wherein the first diameter is smaller than the third diameter by at least 25%.

12. The method of claim 9, wherein, in the step of mounting the stent in the radially contracted position onto the delivery catheter, radial contraction of the delivery catheter occurs.

13. A method of loading a stent on a delivery catheter, the delivery catheter having a proximal end and a distal end, the method comprising:

providing a stent having a length, at least a portion of the length of the stent being in a radially contracted position, the stent capable of being dilated from the radially contracted position to a radially expanded position, the stent having a first diameter in the radially contracted position and a second diameter in the radially expanded position, the second diameter being greater than the first diameter;

providing the delivery catheter;

providing a conical sheath disposed about the proximal end of the delivery catheter;

sliding the stent in the radially contracted position over and past the conical sheath onto the delivery catheter, the stent being maintained in a stationary position while moving the delivery catheter, and wherein radial contraction of the delivery catheter occurs.

* * * * *